(12) United States Patent
Waterman et al.

(10) Patent No.: US 6,693,613 B2
(45) Date of Patent: Feb. 17, 2004

(54) ASYMMETRIC LIQUID CRYSTAL ACTUATION SYSTEM AND METHOD

(75) Inventors: John Karl Waterman, Mesa, AZ (US); Jason Wellman, Scottsdale, AZ (US)

(73) Assignee: Three-Five Systems, Inc., Tempe, AZ (US)

( * ) Notice: Subject to any disclaimer, the term of this patent is extended or adjusted under 35 U.S.C. 154(b) by 190 days.

(21) Appl. No.: 09/862,075

(22) Filed: May 21, 2001

(65) Prior Publication Data

US 2002/0180674 A1 Dec. 5, 2002

(51) Int. Cl.[7] ................................................. G09G 3/18
(52) U.S. Cl. ........................................... 345/87; 345/53
(58) Field of Search ............................. 345/87, 94, 89, 345/92, 97, 96, 100, 98, 99, 208, 209; 340/984, 805; 359/56

(56) References Cited

U.S. PATENT DOCUMENTS 5,583,533 A * 12/1996 Moriyama .................. 345/94
5,920,301 A * 7/1999 Sakamoto et al. ............ 345/96
2001/0040569 A1 * 11/2001 Liang ......................... 345/212

* cited by examiner

Primary Examiner—Vijay Shankar
Assistant Examiner—Nitin Patel
(74) Attorney, Agent, or Firm—Baker Botts L.L.P.

(57) ABSTRACT

A liquid crystal display (LCD) system, comprising a matrix of pixels, actuates each pixel by applying positive and negative voltage differences across a liquid crystal layer. The liquid crystal layer is parallel to a transparent cover. The transparent cover is adjacent to a cover electrode. Each pixel includes a pixel electrode positioned on the opposite side of the liquid crystal layer from the cover electrode. The positive and negative voltage differences are asymmetric to compensate for polarity-dependent characteristics of the LCD materials. The positive and negative voltage differences are applied for durations that counterbalance the asymmetric rates of charge accumulation.

10 Claims, 8 Drawing Sheets

US 6,693,613 B2

ASYMMETRIC LIQUID CRYSTAL ACTUATION SYSTEM AND METHOD

RELATED APPLICATIONS

The present invention is related to the subject matter disclosed in pending U.S. application Ser. No. 09/685,834, which is hereby incorporated by reference in its entirety.

FIELD OF THE INVENTION

The present invention relates generally to liquid crystal display (LCD) devices, and more particularly to a system and method for asymmetrically actuating a liquid crystal display.

BACKGROUND OF THE INVENTION TECHNOLOGY

Liquid crystal displays (LCDs) are commonly used in devices such as portable televisions, portable computers, control displays, and cellular phones to display information to a user. LCDs act in effect as a light valve, i.e., they allow transmission of light in one state, block the transmission of light in a second state, and some include several intermediate stages for partial transmission. When used as a high resolution information display, as in one application of the present invention, LCDs are typically arranged in a matrix configuration with independently controlled display areas called "pixels" (the smallest segment of the display). Each individual pixel is adapted to selectively transmit or block light from a backlight (transmission mode), from a reflector (reflective mode), or from a combination of the two (transflective mode).

An LCD pixel can control the transference for different wavelengths of light. For example, an LCD can have pixels that control the amount of transmission of red, green, and blue light independently. In some LCDs, voltages are applied to different portions of a pixel to control light passing through several portions of dyed glass. In other LCDs, different colors are projected onto the area of the pixel sequentially in time. If the voltage is also changed sequentially in time, different intensities of different colors of light result. By quickly changing the wavelength of light to which the pixel is exposed an observer will see the combination of colors rather than sequential discrete colors. Several monochrome LCDs can also result in a color display. For example, a monochrome red LCD can project its image onto a screen. If a monochrome green and monochrome blue LCD are projected in alignment with the red, the combination will be a full range of colors.

LCDs are actuated pixel-by-pixel, either one at a time or a plurality simultaneously. A voltage is applied to each pixel area by charging a capacitor formed in the pixel area. The liquid crystal responds to the voltage across the pixel by twisting and thereby transmitting a corresponding amount of light. In some LCDs an increase in the actuation voltage decreases transmission, while in others it increases transmission. When multiple colors are involved for each pixel, multiple voltages are applied to the pixel at different positions (different capacitance areas of a pixel being charged) or at different times depending upon the LCD illumination method. Each voltage controls the transmission of a particular color. For example, one pixel can be actuated for only blue light to be transmitted while another for green light, and a third for red light. A greater number of different light levels available for each color results in a much greater number of possible color combinations. Colors may be combined from a red pixel, a green pixel and a blue pixel, each residing on a different LCD, to produce any desired combined pixel color. The three LCDs (red-green-blue or RGB) are optically aligned so that the resulting light from each of the corresponding RGB pixels produces one sharp color pixel for each of the pixels in the LCD pixel matrices. The array of programmed pixels constitutes one video frame. A sequence of video frames produces video images that may change over time (e.g., motion video).

LCD technology has reduced the size of displays from full screen sizes to minidisplays of less than 1.3 inches diagonal measurement, to microdisplays that require a magnification system. Microdisplays may be manufactured using semiconductor integrated circuit (IC) dynamic random access memory (DRAM) process technologies. The microdisplays consist of a silicon backplane, a cover glass and an intervening liquid crystal layer. The microdisplays are conventionally arranged as a matrix of pixels arranged in a plurality of rows and columns, wherein an intersection of a row and a column defines a position of a pixel in the matrix. Each pixel responds to changes in voltage by changing its illumination characteristics. If electrical charge has been built up at a pixel, however, a change in voltage may not change the illumination characteristics as quickly as desired. This phenomenon this called "sticking". It is desirable for pixels of a microdisplay to be actuated so that a series of images corresponding to received image information is viewable on the microdisplay without sticking or flicker.

SUMMARY OF THE INVENTION

The present invention reduces the above-identified problems as well as other shortcomings and deficiencies of existing technologies by providing a system and method for improving image quality of a liquid crystal display (LCD) by asymmetrically actuating pixels of the display.

In a system embodiment of the present invention, a liquid crystal display includes a transparent cover. A cover electrode is positioned adjacent to the cover. A liquid crystal layer is positioned parallel to the cover. On the opposite side of the liquid crystal layer from the cover electrode are pixel electrodes arranged in a matrix of rows and columns. The positions of the pixel electrodes define portions of the liquid crystal display referred to as pixels. A control circuit receives digital video information at an input. The digital video information is sufficient to determine states of individual pixels. The control circuit generates first and second actuation voltages for at least one pixel from the digital video information. First and second voltages for the cover electrode are also generated such that the absolute difference between the first cover electrode voltage and the first actuation voltage is different from the absolute difference between the second cover electrode voltage and the second actuation voltage, the differences are asymmetric. The first cover electrode and actuation voltages are applied to the cover electrode and pixel electrode respectively for a first period of time. The second cover electrode and actuation voltages are applied to the cover electrode and pixel electrode respectively for a second period of time. The ratio of the first period of time and the second period of time correspond to the asymmetric variance of the actuation voltages whereby charge is not built up on the microdisplay. In a more particular embodiment, the first and second cover electrode voltages are identical. In another more particular embodiment, the first actuation voltage is greater than the first cover electrode voltage and the second actuation voltage is less than the second cover electrode voltage. In another more particular embodiment, the control circuit generates a plurality of first actuation voltages as a positive frame and a plurality of second actuation voltages as a negative frame.

In a method embodiment of the present invention, a cover voltage is applied to the cover electrode in a liquid crystal display. Voltages greater than and less than the cover voltage are sequentially applied to pixel electrodes corresponding to pixels in a first region of pixels. The voltages sequentially applied to the first region have a first average voltage. Voltages greater than and less than the cover voltage are sequentially applied to pixel electrodes corresponding to pixels in a second region of pixels. The voltages sequentially applied to the second region have a second average voltage that is different from the first average voltage. An input is received that selects one of at least the first region and the second region. A new cover voltage is determined based at least in part on the average voltage of the region selected by the input. In a more particular embodiment of the invention, the regions include numbers and the input is received from a remote control having buttons with the indicated numbers.

A technical advantage of the present invention is that it controls the light level of pixels of a liquid crystal display. Another technical advantage of the present invention is that it can actuate pixels with different voltage magnitudes for different polarities to offset variations in electropositivity of the display materials and reduce flicker. Another advantage of the present invention is that it allows manual calibration of the cover electrode voltage after manufacture. Another technical advantage of the present invention is that is can reduce charge build up and resultant image sticking.

Other technical advantages of the present disclosure will be readily apparent to one skilled in the art from the following figures, descriptions, and claims. Various embodiments of the invention obtain only a subset of the advantages set forth. No one advantage is critical to the invention. For example, one embodiment of the present invention may only provide the advantage of controlling the pixels of a liquid crystal display, while other embodiments may provide several of the specified and apparent advantages.

BRIEF DESCRIPTION OF THE DRAWINGS

A more complete understanding of the present disclosure and advantages thereof may be acquired by referring to the following description taken in conjunction with the accompanying drawings, wherein.

Figure 1:
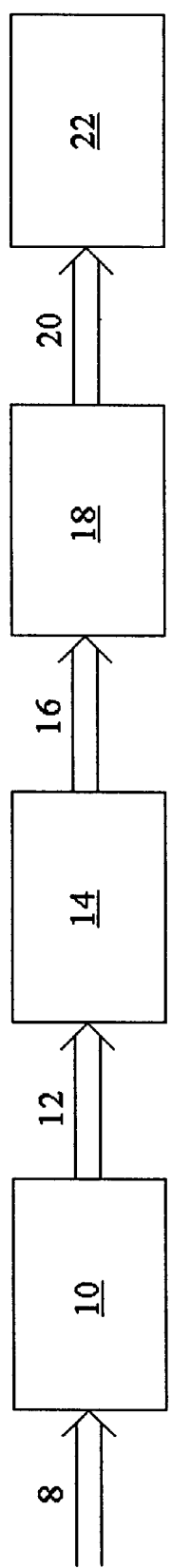
FIG. 1 is a block diagram of a liquid crystal display actuation system.

While the present invention is susceptible to various modifications and alternative forms, specific exemplary embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

The present invention is directed to a liquid crystal display (LCD) comprising a matrix of liquid crystal pixels having light modifying properties controlled by voltage values stored in capacitors formed by electrodes located in the matrix of pixels of the LCD. The voltage inputs to the LCD pixels are analog signals with values sequentially above and below a reference or cover voltage of typically from about 7.5 to 8.0 volts. That reference voltage is called "VCOM" and connects to the LCD cover glass electrode which is a transparent conductive coating on the inside face (liquid crystal side) of the cover glass. The transparent conductive coating is typically Indium Tin Oxide (ITO). The video inputs are connected across the liquid crystal cell from the cover glass electrode such that a potential difference is applied across the liquid crystal cell.

Alternate frames of video pixels are run at voltages above the center reference or cover voltage (positive inversion) and below the center reference or cover voltage (negative inversion). The voltage difference, whether positive or negative, determines that amount of light able to traverse the pixel. Alternating between positive and negative inversions results in a zero net DC bias at each pixel. This can help reduce the "image sticking" phenomena. Asymmetric inversions where the positive voltage difference does not match the negative voltage difference will result in a non-zero net DC bias at each pixel, if the time periods during with those voltage differences are applied are equal. If the time periods of application counterbalance the asymmetric voltages, e.g., the higher voltage difference is maintained for a shorter period of time than the lower voltage difference, a zero net DC bias can be achieved at each pixel.

Referring now to the drawings, the details of preferred embodiments of the invention are schematically illustrated. Like elements in the drawings will be represented by like numbers, and similar elements will be represented by like numbers with a different lower case letter suffix.

FIG. 1 depicts a high-level block diagram of a system for actuating pixels of a liquid crystal display screen in accordance with video data. FIG. 1 illustrates one exemplary embodiment of the present invention. A video software program 10 accesses stored data 8 representing an image or series of images. The video software program 10 locates pixel-specific information in the stored data 8 according to its protocol. For example, the data may be stored in Apple Corporation's Quicktime format, Microsoft Corporation's Media Player format, or the MPEG-2 standard format. The video software outputs pixel-specific digital data for one or more colors 12. For example, the pixel-specific data may include 8-bits for each of red, green, and blue. A signal that can be referred to as an RGB signal. In another embodiment, the software program 10 receives video data directly from an optical recording device such as a video camera.

The pixel-specific data 12 corresponds to the settings of the video software 10 and the contents of the stored data 8 (or the optical recording device), but is not necessarily consistent with the physical characteristics of the liquid crystal display 22. The pixel-specific data 12 is received by image rescaling and frame rate conversion electronics 14. The conversion electronics 14 converts the pixel-specific data 12 so that the number of rows, the number of columns, and the number of images to be displayed in a set amount of time correspond to the capabilities of the liquid crystal display. The conversion electronics 14 outputs modified pixel-specific data 16. In an alternate embodiment, a real time source of video data, such as a video camera, can be configured to provide pixel-specific video data 16 without a need for a software program 10 or conversion electronics 14.

The pixel-specific data 16 is received by liquid crystal display driver electronics 18. The driver electronics 18 converts the pixel-specific data 16 from digital form to pixel-specific voltages in analog form. In one embodiment, a single voltage source for each pixel drives a monochrome display. In another embodiment, a pixel has several voltages each for a different color, sequentially applied, in order to drive a full color display. Driver electronics 18 can be provided for each color for which there is pixel-specific data 16. The driver electronics then provides those pixel charging voltages and control signals 20 to the liquid crystal display 22. The pixel-charging voltages each correspond to one pixel of one image. The control signals are used by the liquid crystal display for several functions, including to match the voltages to their pixels, to provide a comparison voltage for the pixel charging voltages, and to provide a voltage for charging pixels outside the image.

The liquid crystal display 22 applies voltages to individual pixels and, in some embodiments, to particular colors for each pixel. The liquid crystal display 22 selects pixels to which to apply voltages in accordance with received control signals. The voltages change the light transfer characteristics of the pixels. The collective visual impact of the selectively lighted pixels portrays an image.

Figure 2:
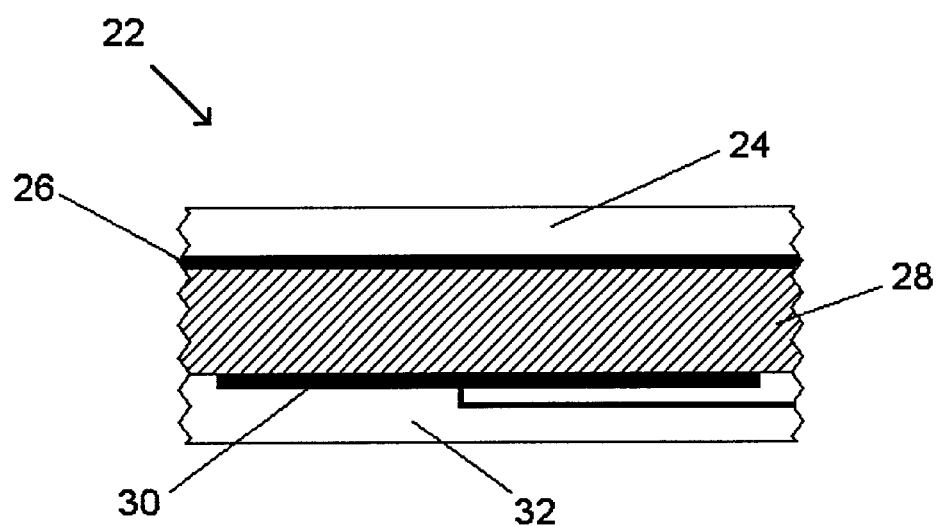
FIG. 2 is a cross-sectional view of a liquid crystal display pixel.

FIG. 2 depicts a cross-sectional view of a single pixel 22 in the matrix in one exemplary embodiment of the present invention. To incident light, the pixel 22 is a liquid crystal layer 28 above a reflecting mirror 30. The transparent cover 24 is chosen to affect the light as little as possible. By changing the liquid crystal state, the incident light can be made to change its polarization. The silicon backplane 32 supports the array of pixels, 10 to 20 microns in pitch. Each pixel 22 has a mirrored surface 30 that occupies most of the pixel area. Each mirrored surface 30 is also a pixel electrode that forms a pixel capacitor with the indium tin oxide (ITO) layer 26 as the other plate of the pixel capacitor. The ITO layer is also referred to as the cover electrode 26. The ITO layer 26 can be a coating on the transparent cover 24 and is common to all pixel capacitors in the matrix of pixels. As the pixel capacitor is charged to a certain pixel value by placing different voltages on the electrodes, the liquid crystal layer 28 between the plates of the pixel capacitor "twists" or "untwists" which affects the polarization of the light incident to the pixel 22 (reflections from the pixel mirrors).

The choice of voltage, VCOM, to place on the ITO layer 26 depends on conditions in which the LCD will be used. A level of VCOM that reduces image sticking by the greatest extent in one application may not be the choice the reduces it most in another application. In addition, the use of positive and negative video frames, relative to VCOM, may create flickering. For example, a positive voltage across a liquid crystal cell may result in a slightly different level of light transfer than a negative voltage of the same magnitude. Such differences can result from the material characteristics of the display. Different voltage magnitudes, asymmetric voltages, can be used for positive and negative frames to accommodate such differences and reduce flickering. For example, a different voltage can be placed on the mirrors 30 or the VCOM can be modified. In order to avoid a net build up in charge that can then cause images to stick, the timing of the positive and negative frames must also be asymmetric.

Figure 3:
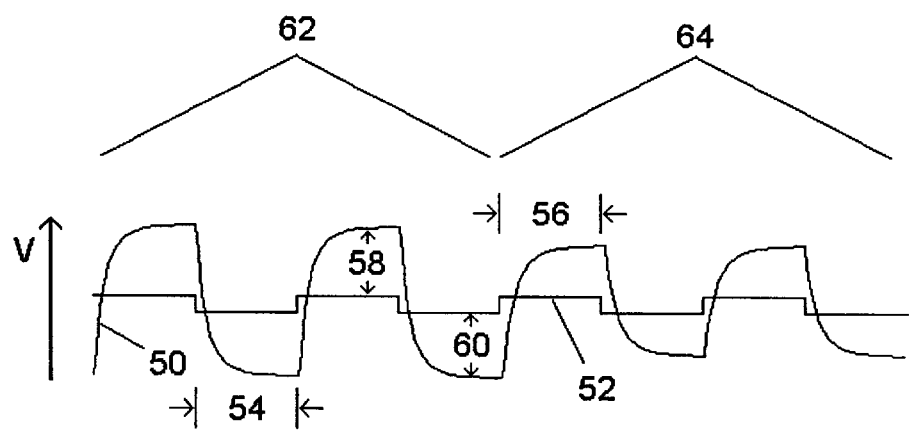
FIG. 3 is a graph of liquid crystal display actuation system voltages over time.

FIG. 3 depicts an example of voltages applied to a single pixel by an exemplary embodiment of the invention. The pixel electrode voltage 50 varies between positive and negative frames. In one embodiment, the VCOM 52, which is placed on the ITO layer 26, is modified between the positive and negative frames, but generally by much less than the pixel electrode voltage 50. The positive frame voltage difference 58 determines the affect of the liquid crystal layer 28 on the incident light during the positive frame. The negative frame voltage difference 60 determines the affect of the liquid crystal layer 28 on the incident light during the negative frame.

In order to compensate for material characteristics, the magnitude of the positive frame voltage difference 58 can be set at a different level from the magnitude of the negative frame voltage difference 60. The different magnitudes will result in charge being accumulated on the capacitor at different rates during the positive and negative frames. The positive frame duration $T_{POS}$ 56 and the negative frame duration $T_{NEG}$ 54 are set to counterbalance those different rates such that the total charge accumulation for both the positive frame and the negative frame is zero. For example, if the liquid crystal layer 28 reacts more strongly to a positive voltage difference, then having a lesser magnitude of positive frame voltage difference 58 as compared to negative frame voltage difference 60 can reduce flicker by preserving the light transfer characteristics of the liquid crystal layer 28 between frames. In order to prevent charge buildup in the example, $T_{POS}$ 56 would be increased relative to $T_{NEG}$ 54. This would allow an equal and opposite amount of charge movement during the positive and negative frames, so that no charge accumulation occurs and image sticking is avoided.

When the digital video data for a new frame indicates a new value for a particular pixel, new voltages differences 58, 60 are applied by varying the pixel electrode voltage 50 maximums. For example, the charts depicts a first pixel state 62 maintained for two positive-negative frame cycles and a second pixel state 64, having smaller magnitude voltage differences, maintained for two positive-negative frame cycles. The decreased voltage difference across the liquid crystal layer 28 during the second pixel state 64 can result in either an increase or a decrease in the transmitted light, depending upon the characteristics of the transparent cover 24 and reflective surface 30.

Figure 4:
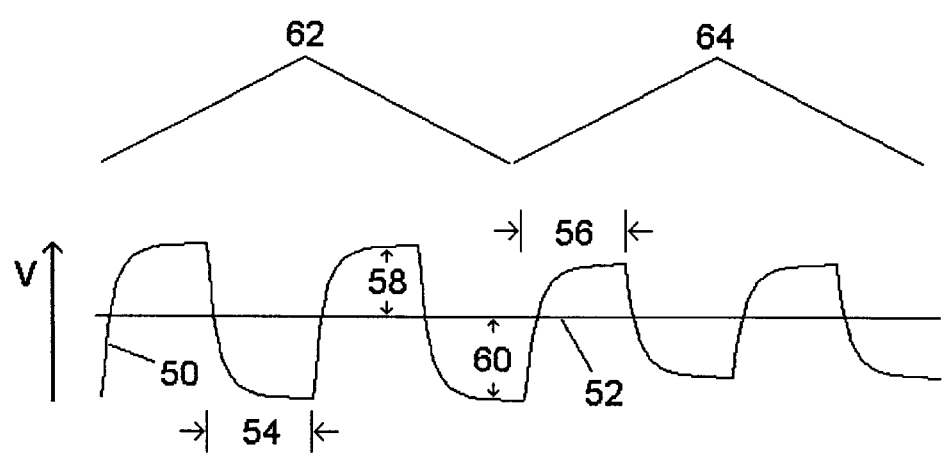
FIG. 4 is a graph of liquid crystal display actuation system voltages over time in another embodiment of the invention.

FIG. 4 depicts an example of voltages applied to a single pixel by another exemplary embodiment of the invention. In this embodiment, the VCOM 52 is kept at the same voltage during both positive and negative frames. The negative frame voltage difference 60 is shown having a greater magnitude than the positive frame voltage difference 58 for both the first pixel state 62 and the second pixel state 64, because the pixel electrode voltage 50 varies more toward lower voltages. For example, VCOM 52 can be set at 8 volts with the pixel electrode voltage 50 varying between 1.5 volts and 14 volts for the first pixel state 62 and varying between 4.75 and 11 volts for the second pixel state 64. In order to reduce charge accumulation the $T_{POS}$ 56 and $T_{NEG}$ 54 would be set to counterbalance the change in magnitude of voltage difference in positive and negative frames as discussed above with respect to FIG. 3.

Figure 5:
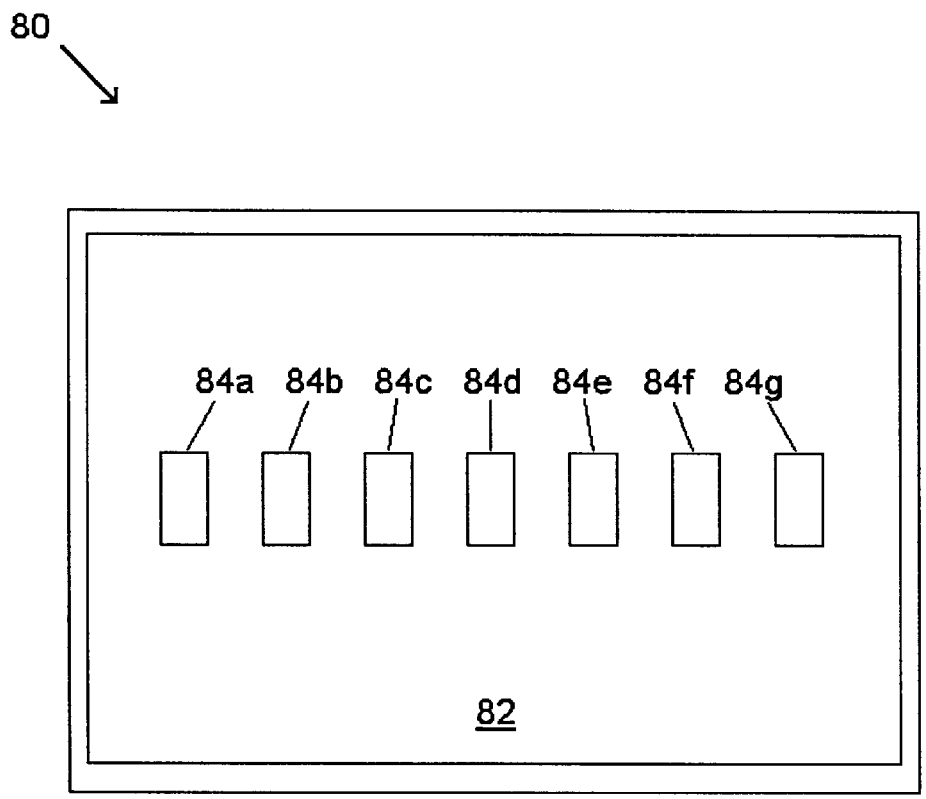
FIG. 5 is a front view of a liquid crystal display while a method embodiment of the present invention is performed.

FIG. 5 is a front view of a liquid crystal display while a method embodiment of the present invention is performed.

The display device 80 can be a television, computer monitor, or other display device. The liquid crystal display 82 is the screen on which images will be displayed. Asymmetric actuation of the liquid crystal display 82 can be used to calibrate the VCOM for the display. Different regions 84a–g are asymmetrically actuated to simulate the sticking that will result from different levels of VCOM.

For example, VCOM is set at 8 volts. The pixel electrodes for the pixels in each region are assigned the following positive and negative frame voltages:

| Region | Positive | Negative |
|---|---|---|
| 84a | 13.7 v | 1.7 v |
| 84b | 13.8 v | 1.8 v |
| 84c | 13.9 v | 1.9 v |
| 84d | 14 v | 2 v |
| 84e | 14.1 v | 2.1 v |
| 84f | 14.2 v | 2.2 v |
| 84g | 14.3 v | 2.3 v |
| Background | 10 v | 6 v |

Once the pixels in the regions 84a–g have been sequentially actuated through many positive and negative frames, the pixel electrodes in all of the regions are returned to the background actuation of 10 v and 6 v. An observer can determine which of the regions 84a–g experiences the least image sticking. Additional equipment will allow an input identifying the least sticking region. For example, the regions can include numbers or other symbols identifying each one and a remote control can be used to indicate the symbol or buttons or other controls on the display device 80 can be used. If the display device is touch sensitive, a wand or finger could be touched to the location of the region.

Once a region is indicated, the VCOM for the liquid crystal display 82 or the positive/negative cycle timing can be modified to reduce sticking. For example, an input is received indicating that the least sticking occurred for a region whose average pixel electrode voltage was 8.1 volts. That indicates that a larger magnitude of positive cycle voltage difference than negative was necessary to reduce charge accumulation. The increase in positive cycle voltage difference can be directly implemented by reducing VCOM, for example reducing VCOM to 7.9 volts. In an alternate embodiment, the $T_{POS}$ could be increased relative to the $T_{NEG}$ so that charge movement balances even with the lower positive cycle voltage difference.

Figure 6:
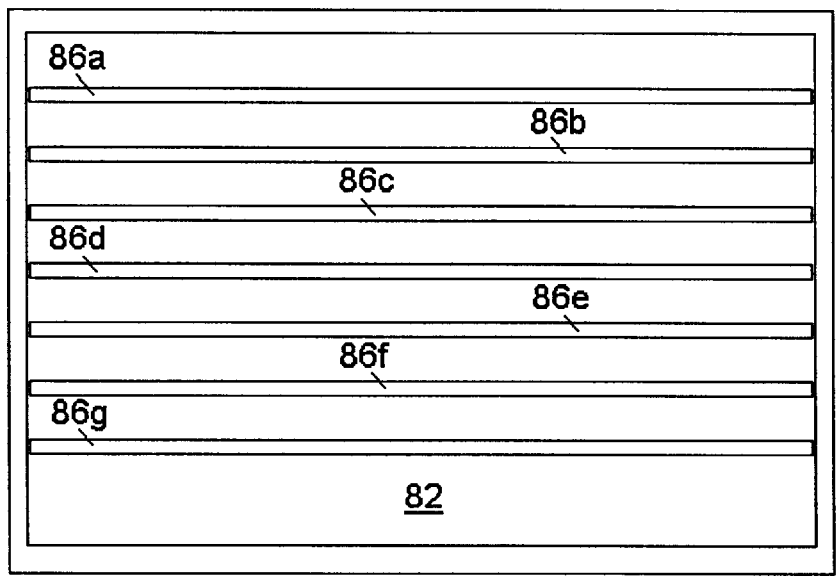
FIG. 6 is a front view of a liquid crystal display while another method embodiment of the present invention is performed.

FIG. 6 is a front view of a liquid crystal display while another method embodiment of the present invention is performed. The display device 80 include a liquid crystal display 82 as a screen. Multiple regions 86a–g are defined on the screen and each region corresponds to pixels in one or more rows. Instead of varying the actuation voltage average for each region, the ratio of $T_{POS}$ to $T_{NEG}$ is varied for regions with consistent actuation voltages. After sequential actuation the pixel electrodes are returned to VCOM and the region images fade as an function of the charge accumulated. As with FIG. 5, an input is then received selecting one of the regions as the region with the least image sticking. A modification of the $T_{POS}$ to $T_{NEG}$ ratio or the VCOM can then be implemented as discussed with respect to FIG. 5. Such calibration can occur as many times as necessary and at different degrees of specificity. For example, a second calibration could occur with voltage averages or $T_{POS}$ to $T_{NEG}$ ratios that vary to a lesser degree around the value chosen in the first calibration.

Figure 7:
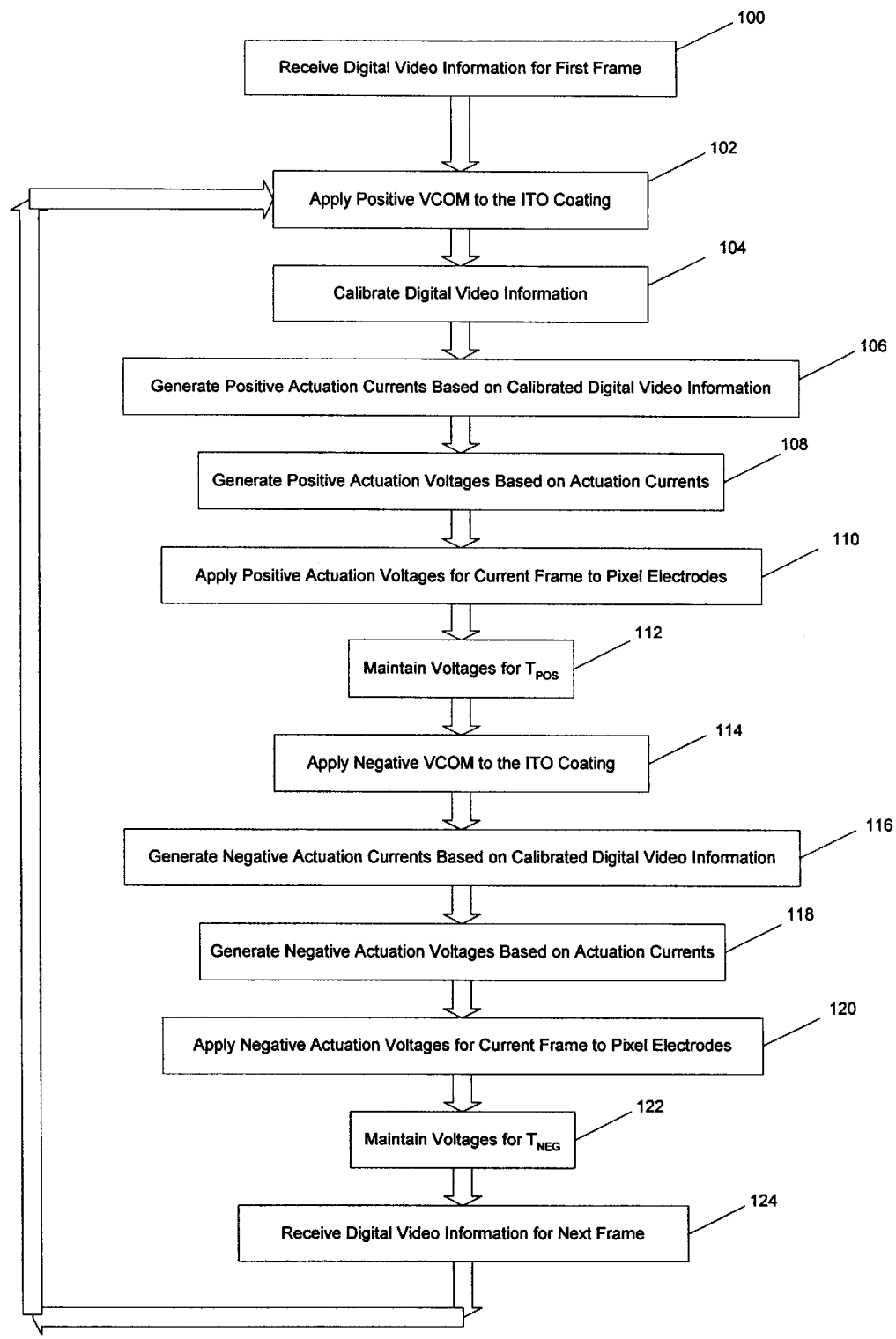
FIG. 7 is a schematic flow diagram of an exemplary embodiment of the invention.

FIG. 7 depicts a schematic flow diagram of an exemplary embodiment of the invention. In the first step 100, a first frame of digital video information is received. In the second step 102, the positive cycle VCOM is applied to the ITO coating or other cover electrode. In the third step 104, the digital video information is calibrated 104. Such calibration can include reformatting for a different resolution, a different number of frames per second, or the voltage sensitivity of the liquid crystal layer 28 among others. In the next step 106, an actuation current for the positive frame cycle is generated for one or more pixels based on the calibrated digital video information. In the next step 108, positive cycle actuation voltages are generated based on the actuation currents. In the next step 110, the positive cycle actuation voltages are applied to pixel electrodes. The positive VCOM and positive cycle actuation voltages are maintained for the positive cycle duration $T_{POS}$ 112.

Similar steps are taken for the negative frame cycle. In the first step 114 of the negative frame cycle, the negative cycle VCOM is applied to the ITO coating or other cover electrode. In the next step 116, an actuation current for the negative frame cycle is generated for one or more pixels based on the calibrated digital video information. In the next step 118, negative cycle actuation voltages are generated based on the actuation currents. In the next step 120, the negative cycle actuation voltages are applied to pixel electrodes. The negative VCOM and negative cycle actuation voltages are maintained for the negative cycle duration $T_{NEG}$ 122. The digital information for the next frame is then received 124 and the positive cycle for the next frame begins. The steps do not have to be performed in strict time order. For example, digital video information for a frame may be calibrated well prior to showing that frame.

Figure 8:
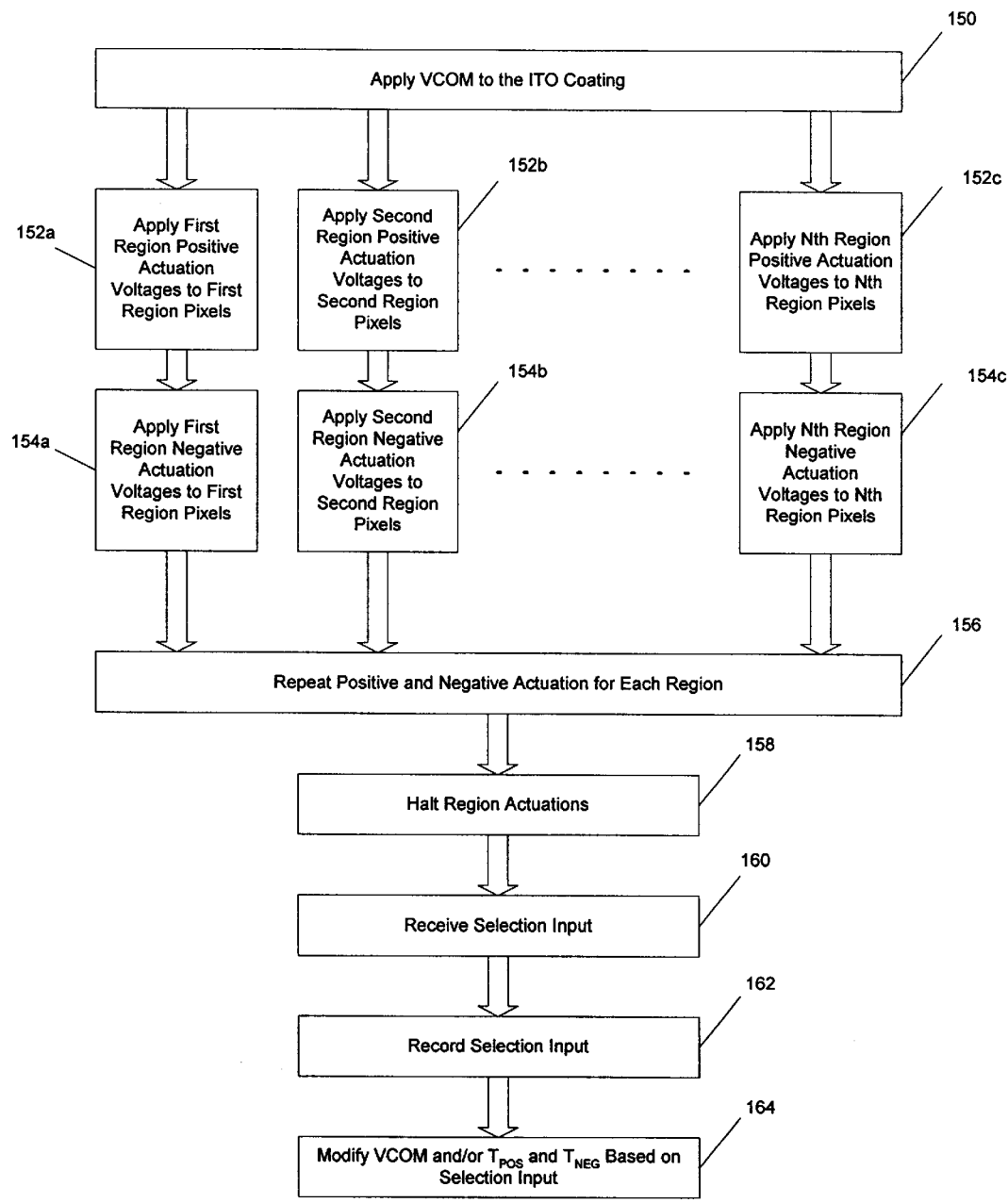
FIG. 8 is a schematic flow diagram of another exemplary embodiment of the invention.

FIG. 8 depicts a schematic flow diagram of another exemplary embodiment of the invention. The ITO coating or other cover electrode is conductively connected to the VCOM voltage 150. Positive actuation voltages are applied to pixel electrodes within a plurality of regions 152a–c. After $T_{POS}$, negative actuation voltages are applied to pixel electrodes within a plurality of regions 154a–c. After $T_{NEG}$, the combination of positive and negative actuation is repeated for the appropriate intervals 156. For each region the average of the positive and negative actuation voltages is different from the other regions. The actuated is then halted 158, and VCOM is again applied to the pixel electrodes. An input selecting a region is received 160. The region selected is recorded 162 and the VCOM or the ratio of $T_{POS}$ to $T_{NEG}$ is modified based on the selected region. In an alternate embodiment, the regions employ differing ratios of $T_{POS}$ to $T_{NEG}$ either in place of or in addition to having differing averages of positive and negative actuation voltages. The method allows for calibration of a liquid crystal display after manufacturing.

It is contemplated and within the scope of the embodiments of the invention that the LCD and/or LCD system may be partially or entirely fabricated on a semiconductor integrated circuit.

The invention, therefore, is well adapted to carry out the objects and attain the ends and advantages mentioned, as well as others inherent therein. While the invention has been depicted, described, and is defined by reference to exemplary embodiments of the invention, such references do not imply a limitation on the invention, and no such limitation is to be inferred. The invention is capable of considerable modification, alternation, and equivalents in form and function, as will occur to those ordinarily skilled in the pertinent arts and having the benefit of this disclosure. The depicted and described embodiments of the invention are exemplary only, and are not exhaustive of the scope of the invention. Consequently, the invention is intended to be limited only by the spirit and scope of the appended claims, giving full cognizance to equivalents in all respects.

What is claimed is:

1. A system for asymmetrically actuating a liquid crystal display (LCD), said system comprising:

a transparent cover;

a cover electrode, positioned adjacent to the cover;

a liquid crystal layer, positioned parallel to the cover;

a matrix of pixel electrodes arranged in a plurality of columns and a plurality of rows, wherein an intersection of a row and a column defines a location of a pixel electrode and a pixel in said matrix, the pixel electrodes positioned on the opposite side of the liquid crystal layer from the cover electrode;

a control circuit including at least one input adapted for receiving digital video information, the digital video information specifying pixel states, the control circuit generating at least first and second actuation voltages corresponding to a pixel state of a pixel from the digital video information;

wherein a first absolute difference between a first cover voltage and the first actuation voltage is different from a second absolute difference between a second cover voltage and the second actuation voltage, the first cover voltage is applied to the cover electrode while the first actuation voltage is applied to one of the pixel electrodes for a first duration, the second cover voltage is then applied to the cover electrode while the second actuation voltage is applied to the same pixel electrode for a second duration; and the ratio of the first duration to the second duration counterbalances the ratio of the first absolute difference to the second absolute difference;

wherein the control circuit includes a first circuit that converts the digital video information into calibrated digital video information.

2. The system of claim 1, wherein the control circuit includes a second circuit that generates an analog current corresponding to the calibrated digital video information.

3. The system of claim 2, wherein the control circuit includes a third circuit that receives analog currents from the second circuit and generates the first and second actuation voltages.

4. A method for asymmetrically actuating a liquid crystal display (LCD) having pixels, said method comprising the steps of:

(a) applying a first cover voltage to a first electrode of a liquid crystal display pixel;

(b) applying a first actuation voltage to a second electrode of the liquid crystal display pixel;

(c) maintaining the first cover voltage and the first actuation voltage at the respective electrodes for a first duration;

(d) applying a second cover voltage to the first electrode of the liquid crystal display pixel;

(e) applying a second actuation voltage to the second electrode of the liquid crystal display pixel, wherein the first difference between the first cover voltage and the first actuation voltage has the opposite polarity as the second difference between the second cover voltage and the second actuation voltage;

(f) maintaining the second cover voltage and the second actuation voltage at the respective electrodes for a second duration, wherein the ratio of the first duration to the second duration counterbalances the ratio of the first absolute difference to the second absolute difference; and (g) converting the digital video information into calibrated digital video information.

5. The method of claim 4, further comprising the step of generating an analog current based on the calibrated digital video information.

6. The method of claim 5, further comprising the step of generating the first and second actuation voltages based on analog currents.

7. A method for asymmetrically actuating a liquid crystal display (LCD) having pixels, said method comprising the steps of:

(a) applying a cover voltage to a cover electrode in the liquid crystal display;

(b) sequentially applying voltages above and below the cover voltage to the pixel electrodes for a first region of pixels, wherein the sequential voltages have a first average;

(c) sequentially applying voltages above and below the cover voltage to the pixel electrodes for a second region of pixels, wherein the sequential voltages have a second average different from the first average;

(d) receiving an input selecting one of at least the first region and the second region;

(e) choosing a new cover voltage based on the average corresponding to the region selected; and (f) sequentially applying voltages above and below the cover voltage to the pixel electrodes for a third region of pixels, wherein the sequential voltages have a third average greater than both the first average and the second average, and wherein the first, second, and third regions are positioned in order and in a linear formation on the liquid crystal display, and the step of receiving an input comprises receiving an input selecting one of at least the first region, the second region, and the third region.

8. A method for asymmetrically actuating a liquid crystal display (LCD) having pixels, said method comprising the steps of:

(a) applying a cover voltage to a cover electrode in the liquid crystal display;

(b) sequentially applying voltages above and below the cover voltage to the pixel electrodes for a first region of pixels, wherein the sequential voltages have a first average;

(c) sequentially applying voltages above and below the cover voltage to the pixel electrodes for a second region of pixels, wherein the sequential voltages have a second average different from the first average;

(d) receiving an input selecting one of at least the first region and the second region;

(e) choosing a new cover voltage based on the average corresponding to the region selected;

(f) displaying a symbol proximate to each region on the liquid crystal display; and (g) generating an electromagnetic signal at a remote control in response to the actuation of a remote control input corresponding to one of the symbols, and wherein the input corresponds to the electromagnetic signal.

9. The method of claim 8, wherein the symbols are numbers.

10. A method for asymmetrically actuating a liquid crystal display (LCD) having pixels, said method comprising the steps of:

(a) applying a cover voltage to a cover electrode in the liquid crystal display;

(b) sequentially applying voltages above and below the cover voltage to the pixel electrodes for a first region of pixels, wherein the sequential voltages have a first average;

(c) sequentially applying voltages above and below the cover voltage to the pixel electrodes for a second region of pixels, wherein the sequential voltages have a second average different from the first average;

(d) receiving an input selecting one of at least the first region and the second region; and (e) choosing a new cover voltage based on the average corresponding to the region selected;

wherein steps b and c occur simultaneously and cease simultaneously and step d occurs after the cessation of steps b and c.

* * * * *